(12) United States Patent
Huang et al.

(10) Patent No.: US 9,814,543 B2
(45) Date of Patent: Nov. 14, 2017

(54) METHODS FOR FABRICATION OF ORTHODONTIC APPLIANCES AND ORTHODONTIC APPLIANCES MADE THEREBY

(71) Applicant: Ormco Corporation, Orange, CA (US)

(72) Inventors: Stanley S. Huang, Irvine, CA (US); Andres Rodriguez, Alhambra, CA (US)

(73) Assignee: Ormco Corporation, Orange, CA (US)

( * ) Notice: Subject to any disclaimer, the term of this patent is extended or adjusted under 35 U.S.C. 154(b) by 384 days.

(21) Appl. No.: 14/180,634

(22) Filed: Feb. 14, 2014

(65) Prior Publication Data

US 2014/0234527 A1 Aug. 21, 2014

Related U.S. Application Data

(60) Provisional application No. 61/765,701, filed on Feb. 16, 2013.

(51) Int. Cl.

| | |
|---|---|
| *C25D 7/06* | (2006.01) |
| *B22C 9/04* | (2006.01) |
| *A61C 7/16* | (2006.01) |
| *A61C 7/20* | (2006.01) |
| *C25D 7/00* | (2006.01) |
| *C25D 1/00* | (2006.01) |

(Continued)

(52) U.S. Cl.

CPC ............... *A61C 7/16* (2013.01); *A61C 7/20* (2013.01); *C25D 1/003* (2013.01); *C25D 5/02* (2013.01); *C25D 5/022* (2013.01); *C25D 5/10* (2013.01); *C25D 7/00* (2013.01); *C25D 7/0607* (2013.01); *C23C 18/1651* (2013.01); *C23C 18/1653* (2013.01); *C25D 5/06* (2013.01); *Y10T 29/49826* (2015.01)

(58) Field of Classification Search
CPC ........ C25D 7/0678; C25D 7/0671; B22C 9/04
USPC ...... 427/2.29, 256, 282; 433/8, 20; 29/896.1, 29/896.11
See application file for complete search history.

(56) References Cited

U.S. PATENT DOCUMENTS

| | | | | |
|---|---|---|---|---|
| 5,018,259 | A | * | 5/1991 | Wildman ............... A61C 7/12 216/33 |
| 6,027,630 | A | * | 2/2000 | Cohen ............... B81C 1/00126 205/118 |

(Continued)

FOREIGN PATENT DOCUMENTS

WO WO 2010151504 A1 * 12/2010

*Primary Examiner* — Cachet I Sellman
(74) *Attorney, Agent, or Firm* — Wood Herron & Evans LLP

(57) ABSTRACT

A method of manufacturing an orthodontic appliance includes plating a first pattern of a material on a substrate to define a layer. Repeating plating of the first material one or more times forms an additional pattern. A layered structure is built up and forms a portion of the orthodontic appliance. A pattern of a second material different from a first material may be plated on the substrate or on a pattern of the first material. The material may be a sacrificial material that may be later removed. The orthodontic appliance may be an archwire or a self-ligating orthodontic bracket having one or more layered structures formed by plating patterns of the material. Plating may include plating patterns of materials so as to form a movable member in place relative to a bracket body.

16 Claims, 11 Drawing Sheets

(51) Int. Cl.
  *C25D 5/02*  (2006.01)
  *C25D 5/10*  (2006.01)
  C25D 5/06  (2006.01)
  C23C 18/16  (2006.01)

(56) References Cited

U.S. PATENT DOCUMENTS

| | | | |
|---|---|---|---|
| 6,071,118 A * | 6/2000 | Damon | A61C 7/287 433/10 |
| 7,384,530 B2 * | 6/2008 | Cohen | B81C 1/00126 205/118 |
| 7,674,110 B2 | 3/2010 | Oda | |
| 8,033,824 B2 | 10/2011 | Oda et al. | |
| 2008/0070184 A1 * | 3/2008 | Farzin-Nia | A61C 7/287 433/9 |
| 2009/0176190 A1 | 7/2009 | Ruiz-Vela et al. | |
| 2012/0148972 A1 * | 6/2012 | Lewis | A61C 7/12 433/10 |
| 2012/0322019 A1 * | 12/2012 | Lewis | A61C 7/20 433/10 |
| 2013/0081271 A1 * | 4/2013 | Farzin-Nia | A61C 13/00 29/896.1 |

* cited by examiner

METHODS FOR FABRICATION OF ORTHODONTIC APPLIANCES AND ORTHODONTIC APPLIANCES MADE THEREBY

CROSS REFERENCE TO RELATED CASES

This application claims priority to U.S. Provisional Patent Application Ser. No. 61/765,701 filed Feb. 16, 2013, the disclosure of which is incorporated by reference herein in its entirety.

TECHNICAL FIELD

The present invention relates generally to methods of making orthodontic appliances by a layering process and to orthodontic appliances made thereby.

BACKGROUND

Orthodontic appliances represent a principal component of corrective orthodontic treatment devoted to improving a patient's occlusion. One type of orthodontic appliance is an orthodontic bracket. Using the orthodontic bracket as an example, an orthodontist may affix orthodontic brackets to the patient's teeth and engage an archwire (another type of orthodontic appliance) into a slot of each bracket. The archwire applies corrective forces that coerce the teeth to move into orthodontically correct positions. Traditional ligatures are often employed to retain the archwire within each bracket slot. Due to difficulties encountered in applying an individual ligature to each bracket, self-ligating orthodontic brackets have been developed that eliminate the need for ligatures by relying on a movable latch or slide for captivating the archwire within the bracket slot. Other orthodontic appliances include palatal expanders, Temporary Anchoring Device (TAD) attachments, bands, torquing springs, and Herbst appliances, among others.

The design, and ultimately the performance, of many of these orthodontic appliances are often limited by the process by which the appliance is manufactured. Generally, manufacturability of an orthodontic appliance is gauged in terms of large quantities (e.g., tens of thousands of units) and to a lesser extent on prototype or testing quantities. But in any respect, the appliance must be capable of being made before it may leave the conceptual stage of development. So, while there may be many theoretical orthodontic appliance designs that may theoretically improve orthodontic treatment, if such a design cannot be brought from within the conceptual world into the real world, and done so at a reasonable cost, it may be abandoned during product development.

Orthodontic appliances are often made in large numbers by manufacturing processes that include metal injection molding (MIM), ceramic injection molding (CIM), casting, and laser sintering (e.g., direct metal laser sintering). However, each of these processes is limiting in a way that restricts the manufacturable appliance design. Thus, many desirable features are not included in the design actually manufactured. Still other processes include machining, stamping, and welding. These other processes also limit the manufacturable orthodontic appliance design.

In particular, in MIM or CIM, metal or ceramic particles, respectively, are mixed with a binder to form a slurry. The slurry is then injected into a mold having the shape of an orthodontic appliance or a component thereof. Similarly, in casting, a molten material (e.g., molten metal) is forced into a mold. Thus, forming an orthodontic appliance or associated component made by any of these processes requires a mold. Use of a mold limits the features of the appliance to those that are formable by and also separable from the mold. Generally, this limits the type and orientation of both internal and external features of the appliance.

Where the feature of the appliance or component is formed by a mold, as opposed to a feature machined into the appliance, the corresponding mold feature must be initially created in the mold surface. There is a lower size limit and minimum level of detail capable of being formed in the mold depending on the method by which the mold is made. Furthermore, the design of the component itself is also restricted by the mold design. For the component to separate from the mold during a demolding process, the component must have a relief or converging aspect that allows the component to be removed from the mold cavity. Otherwise, that is, where there is an interference fit or diverging geometry between the component and the mold, the component would not be removable from the mold cavity. In essence, the component and the mold would be locked together, necessitating destruction of the mold or a portion thereof to release the component. Thus, the use of a mold limits the kind and orientation of features capable of being manufactured.

Additional limitations are associated with use of a mold. For example, the mold design must also incorporate a location for the material to be injected into the mold cavity (e.g., through a gate or other opening) and must also account for how the component, once formed, is removed or ejected from the mold (e.g., via an ejection pin). Any of the above features of the mold may create defects in the component (e.g. flash) that must be removed in a subsequent process. These additional design considerations significantly restrict the features of the component that are ultimately manufactured.

However, alternative geometries that are not capable of being formed during molding may be desirable. The desired geometries may enhance the use and functionality of the orthodontic appliance. For example, certain undercut formations, which include various voids or cavities, may not be capable of being formed in a mold. In some instances, these features may be formed using post-formation processes, such as machining. However, such post-formation processes are generally time consuming and expensive. Still other desirable features are not available at any cost because of the limits imposed by the above-mentioned manufacturing techniques. These desirable features are thus ultimately excluded from a production or real-world design.

In addition, MIM, CIM, and casting processes restrict the materials used in forming the component. Each component manufactured by one of these processes is made by a single shot of a material (e.g. metal particles or ceramic particles or molten material, respectively). The component is consequently made of a single material, though in limited circumstances various inserts may be encapsulated during injection of the slurry or molten material. By contrast, a single component made of multiple materials during a single shot or injection is generally not possible.

A related limitation associated with molding is when the orthodontic appliance is made of multiple components. A multi-component appliance requires assembly following the separate molding of the individual components. Typically this is the situation where various components of the appliance move relative to one another, for example, a self-ligating orthodontic bracket. The molding processes set forth above are not capable of forming the components in their relative assembled configurations. Furthermore, due to the relatively small sizes of the components (often these components are millimeters or fractions of millimeters in size), post-manufacturing assembly can be problematic and may add to the expense of manufacturing the orthodontic appliance.

In addition, in each of the injection molding processes, the component dimensions are difficult to control over both the short term as well as the long term. For example, the green body resulting from a MIM or CIM process is oversized compared to the final product. The green body is sintered to densify the metal or ceramic particles in the slurry. During sintering, the green body shrinks as it approaches a usable or theoretical density. This shrinkage can be affected by any one of a number of variables. Lack of sufficient control of any single variable can cause problems with the dimensions of the component. Thus, producing predictable, consistent shrinkage during production of the component over both the short and long term is difficult. And, due to the number of variables, optimization of the slurry and the mold size requires extensive up-front experimentation. Thus, it may take months before a process for making a new appliance is ready for mass production. Further, once the initial process is established, which provides the desired dimensions, mold wear contributes to reduction in the precision of the desired dimensions over the long term. Accordingly, ongoing maintenance of the molds is necessary to combat mold wear and thus adds to the manufacturing costs.

Other processes used to manufacture orthodontic appliances include rapid prototyping processes, such as, direct metal laser sintering. This process produces components directly from the metal and is essentially a free-form process—no mold is required. In this aspect, many of the problems associated with molds are eliminated. However, rapid prototyping processes still have shortcomings.

Rapid prototyping processes build products on a layer-by-layer basis. The layers are produced in a serial fashion. That is, the layer is produced by tracing a laser over the layer and requires the particles of material to be near the point of intersection between the laser and the layer being formed. The focus point of the laser melts or sinters the particles as the laser traverses along a predetermined path. However, the full layer is not produced until the laser has traversed the entire path for that layer. At any given moment, prior to complete traversal, the layer is only partially formed.

However, rapid prototyping processes introduce unique problems in the manufacture of products made thereby. For one, location of the particles or accuracy of the powder injection with respect to the laser creates dimensional issues. Also problematic is the poor finish quality of the as-formed surface. The poor finish necessitates a subsequent finishing operation. Again, this subsequent operation adds cost to the manufacturing process. In addition, significant thermal gradients develop in the part, often causing distortion in the component or unintended changes in the material phases present in the part.

There is a need, therefore, for a method for manufacturing an orthodontic appliance that addresses these and other problems associated with conventional manufacturing methods. Furthermore, there is a need for a manufacturing method that does not limit orthodontic appliance design. More particularly, there is a need for orthodontic appliances having features that are not capable of being formed in single shot injection molding processes or by rapid prototyping process such that as-yet unmanufacturable design features can be manufactured and then used in the clinical setting.

SUMMARY OF THE INVENTION

In one embodiment, a method of manufacturing an orthodontic appliance comprises plating a first pattern of a first material on a substrate to define a first layer and repeating plating of the first material one or more times to form one or more additional patterns. At least one additional pattern defines a respective layer on at least one of the first layer or on a layer applied subsequent to the first layer to build up a first layered structure that forms at least a portion of the orthodontic appliance.

In one embodiment, the method further comprises plating a second pattern of a second material on the substrate or on the first material. The second material is different from the first material.

In one embodiment, the first material is a sacrificial material and the second material is a structural material. The method further comprises following forming of the first layered structure, removing the sacrificial material whereby the structural material forms the portion of the orthodontic appliance.

In one embodiment, removing the sacrificial material forms at least one of an undercut, an overhang, a recess, or a cavity or a combination thereof in the portion of the orthodontic appliance.

In one embodiment, a perimeter of the first pattern or a perimeter of the one or more additional patterns defines a surface portion of the orthodontic appliance.

In one embodiment, the substrate forms a portion of the orthodontic appliance.

In one embodiment, the orthodontic appliance is an orthodontic pad and the layered structure defines a bonding surface of the pad that is configured to be attached to the surface of a preselected tooth.

In one embodiment, the orthodontic appliance is an archwire that includes a first section adjacent a second section and wherein the layered structure forms the first section and the second section. The first section and the second section are formed at an angle relative to one another. The archwire is configured to fit a predetermined dental arch.

In one embodiment, the orthodontic appliance is an archwire that includes a first section adjacent a second section. The layered structure forms the first section and the second section, each section having a cross sectional shape. The cross sectional shape of the first section is different from the cross sectional shape of the second section in at least one of shape and area.

In one embodiment, the orthodontic appliance is an archwire that includes at least a first section adjacent a second section. The layered structure forms the first section. The method further comprises plating a second pattern of a second material different from the first material on the substrate juxtaposed relative to one of the patterns of the first material. Repeating plating of the second material one or more times forms one or more additional patterns and builds up a second layered structure that forms at least a portion of the second section juxtaposed to the first section.

In one embodiment, the orthodontic appliance is an archwire and plating includes plating each layer in an orientation that is substantially parallel to the longitudinal axis of the archwire.

In one embodiment, the orthodontic appliance is an archwire and plating includes plating each layer in an orientation that is substantially perpendicular to the longitudinal axis of the archwire.

In one embodiment, the orthodontic appliance is a self-ligating orthodontic bracket having at least a bracket body and a movable member. The first layered structure forms at least a portion of the bracket body. The method further comprises plating a pattern of a second material on the substrate or on a pattern of the first material and repeating plating of the second material one or more times to form one or more additional patterns to build up a second layered structure that forms at least a portion of the movable member. Plating patterns of the second material includes plating at least one pattern of the second material in a layer that is common to both of the bracket body and the movable member so as to form the movable member in place relative to the bracket body.

In one embodiment, plating patterns of the second material includes plating patterns of the second material spaced apart from the patterns of the first material.

In one embodiment, the method further comprises plating a sacrificial material between at least one pattern of the first material and at least one pattern of the second material, whereby the first layered structure and the second layered structure are separated by the sacrificial material. The method includes removing the sacrificial material following forming of each of the first and second layered structures.

In one embodiment, the self-ligating orthodontic bracket includes a spring or hinge mechanism and the method further comprises plating a plurality of patterns of a third material. The collective patterns of the third material define a third layered structure that forms the spring mechanism or the hinge mechanism that couples the bracket body to the movable member.

In one embodiment, plating patterns of the third material includes plating at least one pattern of the third material directly in contact with a pattern of the first material and plating at least one pattern of the third material directly in contact with a pattern of the second material such that the third layered structure is in direct contact with each of the first and second layered structures.

BRIEF DESCRIPTION OF THE DRAWINGS

The accompanying drawings, which are incorporated in and constitute a part of this specification, illustrate embodiments of the invention and together with the detailed description given below, serve to explain various aspects of the invention.

DETAILED DESCRIPTION

Figure 1A:
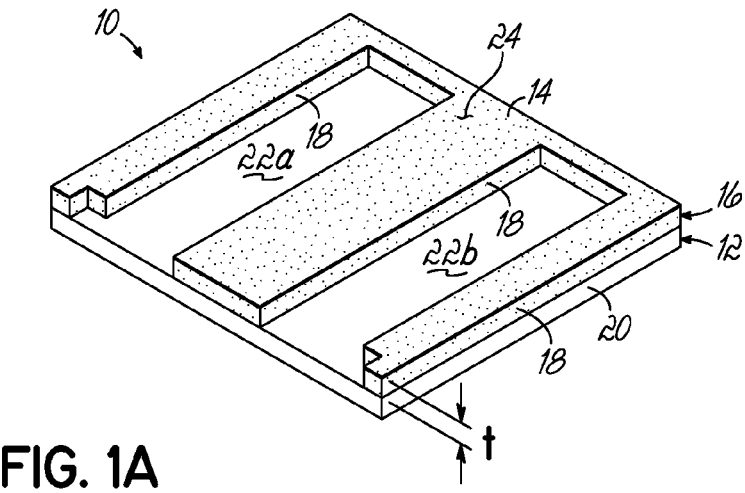
FIG. 1A is a perspective view illustrating a pattern of material plated on a substrate to form a layer according to one embodiment of the invention.

To address these and other shortcomings of existing methods, an orthodontic appliance is made to include a layered structure according to one embodiment of the present invention. Exemplary orthodontic appliances made of or incorporating such a layered structure are shown in FIGS. 2A-6B. As will be described below, a layered structure may be formed of multiple, individual layers stacked one on top of another. The dimension, position, and composition of each layer are predetermined according to a design of a desired orthodontic appliance. Each layer is then stacked in an order specified by its position in the desired design. The individual layers thus collectively form the layered structure.

To this end, according to embodiments of the invention, a computer model or design of the desired orthodontic appliance is initially created. The design is then segregated or "sliced" by digital means or other means into multiple parallel layers. The direction of the slices or layers may be dictated by the design. Each individual layer may be of a substantially uniform thickness. However, the dimensions and composition of each layer may be determined by the location and direction of the layers in the desired design. The layers may therefore be different from one another. The difference between layers may include, for example, a difference in material from which the layer is constructed, a difference in the thickness, a difference in a pattern or shape in the periphery or outline of the materials in the layer, or another measurable difference or a combination of these differences. According to the computer design then, the construction of each layer may be predetermined such that variations in thickness, shape, and/or material between layers may individually or collectively achieve a specific function or form a specific feature of the orthodontic appliance when the layers are stacked together. The orthodontic appliance is manufactured from the layered structure. By varying one or more of the peripheral shape, thickness, and/or material of each layer, the limits of conventional processes described above may be overcome.

Following development of the desired design and slicing the design into predetermined layers as described above, and with reference to FIGS. 1A-1D, a layered structure 10 may be built. According to an initial stage in building or stacking layers to form the layered structure 10, a material is plated onto a substrate 12 in a pattern 14. The pattern 14 of the material may form a layer 16 or a portion thereof, as is described below.

Plating processes are known in the art and, in one embodiment, plating includes forming an adherent layer of the material on the substrate 12 or on a preceding layer (not shown) by means of electrolytic action. In this regard, plating may include exposing the substrate 12 to a plating solution (not shown), which is typically an electrolyte. Plating solutions are known in the art and contain at least one material that is to be incorporated into the layered structure 10, referred to herein as a "structural" material. Additional plating solutions may alternatively contain at least one material that facilitates the formation of the layered structure 10, referred to herein as a "sacrificial" or "support" material, each of which is described in more detail below. As such, multiple plating solutions may be used to sequentially plate different materials onto the substrate 12 to form the layered structure 10.

According to one embodiment, plating includes exposing the substrate to a plating solution, such as, by immersing the substrate 12 in a tank or bath (not shown). Exposing may, however, be achieved by other means that do not require immersion of the substrate 12 in the plating solution, such as, by selective or brush plating as is known in the art.

Once exposed to the solution, in one embodiment, application of an electrical current may cause a selected material to deposit from the solution on the substrate 12. This type of deposition may occur in a substantially uniform manner over an exposed portion of the substrate 12 at the same time. In this regard, by way of example only, plating may include electroplating or electrodeposition. However, plating is not limited thereto and may include electroless plating processes as are known in the plating art. Such processes are known to deposit material by a controlled chemical reduction that is catalyzed by a metal, alloy, or other material being deposited rather than by electrolytic means (e.g., electroplating). So, while the term "plating" may refer to electroplating in any given context, one of ordinary skill will observe that other plating processes, e.g., electroless plating, may also be applicable. In view of the above, the term "plating" as used herein does not encompass deposition from a vapor, for example, by chemical vapor deposition (CVD) or by physical vapor deposition (PVD), or deposition by spray coating, for example, plasma spray, flame spray, or other thermal spray operation. However, a material may be deposited on the layered structure 10 or on a portion thereof by one or more of these processes, or another suitable process. The material deposited thereby may precede, alternate with, and/or follow plating as described herein.

The substrate 12 may be any material that is compatible with the plating process, particularly the plating solution. In one embodiment, the substrate 12 forms a portion of the orthodontic appliance. So, in this case, the substrate 12 may form a portion of the layered structure 10 and must also be compatible with the environment found in a human mouth. In this regard and by way of example, the substrate 12 may be an orthodontic pad for use with an orthodontic bracket body, described more fully below with respect to FIG. 5. It will be appreciated, however, that the substrate 12 may not form a portion of the orthodontic appliance and may be separable from the layered structure 10.

Additionally, while the substrate 12 is shown in FIGS. 1A-1E as having a substantially flat surface on which the layered structure 10 may be built, embodiments of the invention are not so limited. By way of example, the substrate 12 may be a simple curve or a complex structure. In one embodiment, where the substrate 12 is separable from the layered structure 10, the surface of the substrate 12 has a shape that is a near replica of the surface of a patient's tooth. The initial layer of the layered structure 10 may conform nearly exactly to the replica surface and result in a custom fit between one surface of the layered structure 10 and the patient's tooth.

With continued reference to FIG. 1A, the material may be plated in such a manner so as to define the pattern 14. The pattern 14 has at least one defined periphery or perimeter 18 and may be of substantially uniform thickness, t. The pattern 14 of the material may be of nearly any shape and may be formed by exposing preselected portions of the substrate 12 to the plating solution. This may be achieved by exposing only those selected portions of the substrate 12 to the plating solution where the material is desired. Alternatively, the pattern 14 may be formed by masking the substrate 12 from contact with the solution where it is undesirable for the material to plate. Methods of electroplating by using a mask and associated techniques are disclosed in U.S. Pat. No. 6,027,630, which is incorporated by reference herein in its entirety. In addition, methods of electroplating are known in the art, such as, the MICA Freeform™ process that is commercially available from Microfabrica Inc. of Van Nuys, Calif.

The perimeter 18 of the pattern 14 may conform along its outer edge to the periphery or perimeter 20 of the substrate 12 and may cover the entire exposed surface of the substrate 12. It will be appreciated, however, that embodiments of the present invention are not limited to patterns that cover the entire surface of the substrate 12 or conform to the substrate 12 either in whole or in any particular part. In other words, the pattern 14 and the shape of the substrate 12 may be unrelated. By way of example, the pattern 14 may extend or conform to one or more edges or a portion of an edge of the substrate 12, as shown in FIG. 1A. Alternatively, the pattern 14 may be completely within the perimeter 20 of the substrate 12. That is, the perimeter 18 of the pattern 14 may not extend to any edge of the substrate 12. As such, there may be numerous layered structures on each substrate, depending on the respective sizes of the substrate 12 and the layered structure 10. The thickness, t, of the pattern 14 may be as thin as about 20 µm. However, thinner and thicker patterns may be possible. For example, the thickness of any particular pattern may be as much as 1.25 mm. Such thicknesses may enable single layered structures, for example, orthodontic pads, to be formed. The thickness of any particular pattern may be determined by the thickness of a mask, when implemented, and the conditions used to plate the material, among other variables.

The pattern 14 may define one or more exposed areas 22a, 22b where the substrate 12 is not significantly covered by the pattern 14. The exposed areas 22a, 22b may be surrounded or defined in part by the pattern 14 and possibly by one or more edges of the substrate 12, as shown. For example, the pattern 14 may define a circular exposed area. Thus, the pattern 14 may have an annular shape. The exposed areas 22a, 22b are not limited to any particular size, shape, or number and may be determined by the shape and size of any mask that is used during plating of the pattern 14 of the material.

Although not shown in FIG. 1A, plating of the material may be repeated to form one or more additional patterns on the layer 16. A layered structure thus formed may appear to be homogenous. Each additional layer may include a different pattern from pattern 14, though the different patterns may be limited to those that only extend to the perimeter of the immediately preceding pattern. That is, the patterns of subsequent layers may not overhang or extend beyond the perimeter 18 of pattern 14. In one embodiment, the layered structure 10 may be made of a single material with each layer of the material plated in direct contact with the layer subsequent to the first layer and extending only so far as the perimeter of the pattern of the preceding layer. By way of example, such a layered structure may be configured as an orthodontic pad for use with a bracket body as is described with respect to FIG. 5, below.

Figure 1B:
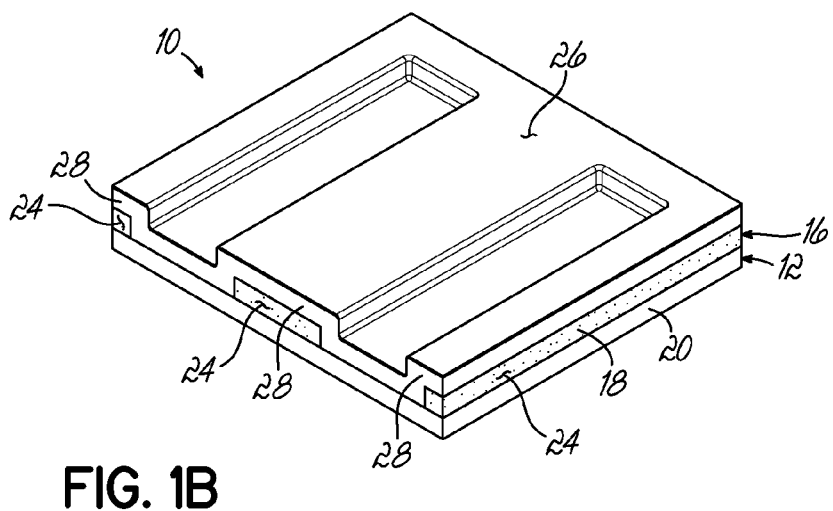
FIG. 1B is a perspective view illustrating the layer of FIG. 1A with a second material plated over the pattern.
Figure 1C:
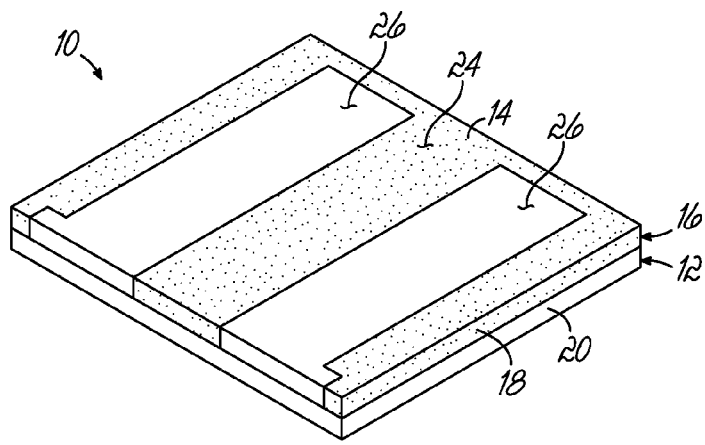
FIG. 1C is a perspective view illustrating the result of removing a portion of the second material shown in FIG. 1B to form a layer of two materials.

With reference now to FIGS. 1B and 1C, in one embodiment, each layer may be made of multiple materials. Use of multiple materials enables unique features to be formed in the layered structure 10 and ultimately in an orthodontic appliance. For example, as shown in FIG. 1C, the layer 16 may include two different materials. However, unless indicated otherwise, reference to a "first" material, a "second" material, or a "third" material does not mean that the materials are different. To the contrary, as is set forth in detail below with respect to orthodontic appliances having multiple parts, each part may be the same material though one part may be made of a "first" material and another part is made of a "second" material and yet another part is made of a "third" material.

In one embodiment, the two materials include a sacrificial material 24 and a structural material 26. The structural material 26 is one that forms a portion of an orthodontic appliance. Structural materials may include those normally used in orthodontic applications including metals, ceramics, and polymers. Still other structural materials may include semiconducting materials. By way of further example, metals may include titanium, gold, silver, cobalt, rhodium, and palladium or alloys containing one or more of these metals. Specific alloys may include titanium alloys, stainless steels, cobalt-nickel alloys, and nickel-titanium alloys. However, other metals capable of being plated are known in the art and may be used as a structural material according to embodiments of the present invention. Any single layer may include multiple different patterns of structural materials as described below.

By contrast, the sacrificial material 24 may not be included in the orthodontic appliance, with the exception that residual amounts of the sacrificial material may remain in or on the orthodontic appliance. Sacrificial materials may include materials that melt, dissolve, or are etched under conditions that do not appreciably affect the structural material and, optionally, the substrate of the layered structure 10. Sacrificial materials include metals, such as, copper or copper alloys or other low melting point, though often conductive, materials. Accordingly, the sacrificial material 24 may be removed following formation of the layered structure 10, as described below. It will be appreciated that multiple different sacrificial materials may be included in a layer. It is noted that where a sacrificial material substantially covers the substrate 12, the layered structure 10 may be more easily separated from the substrate 12 simply by removing the sacrificial material from between the layered structure 10 and the substrate 12.

In the situation where the pattern 14, as shown in FIG. 1A, is made of the sacrificial material 24, the structural material 26 may be plated on the sacrificial material 24 by exposing the substrate 12 and the sacrificial material 24 to a different solution. The sacrificial material 26 may then be plated, as shown in FIG. 1B. However, in the embodiment shown in FIG. 1B and unlike plating the pattern 14 of the sacrificial material, the structural material 26 may blanket the pattern 14 and the substrate 12 in the exposed areas 22a, 22b (shown in FIG. 1A). In other words, the structural material 26 may not be initially restricted to any pattern and thus may extend to each edge of the substrate 12 or the coverage may be sufficient to cover only one or more of the exposed areas 22a, 22b of the substrate 12. This type of "blanket plating" often results in areas of overplated material 28 on the pattern 14.

The layer 16 of the sacrificial and structural materials 24, 26, shown in FIG. 1C, may be formed by removing at least a portion of the overplated material 28 shown in FIG. 1B. At least a portion of the structural material 26 plated in the exposed areas 22a, 22b remains after the removal of the excess structural material. It will be appreciated that a portion of the sacrificial material 24 may also be removed during this process. Removing the structural material 26 may include micro-machining or another removal process that planarizes the sacrificial and structural materials into a substantially uniformly thick layer, which may be thinner than thickness, t, of pattern 14. In this manner, the layer 16 includes two materials that are substantially coplanar, as shown. Each material occupies a specific area or region of the layer 16. Thus, blanket plating of a second material over an initial pattern allows the formation of a second pattern. The second pattern may be essentially defined by the first pattern following removal of any excess second material. According to FIG. 1C, the pattern 14 defines the pattern of the structural material 26. Following removal of any overplated material 28, one or more cleaning processes may be used to rid the surface of any residual overplated material or to remove any particulates associated with the removing or planarizing process. Rather than plating a layer including a sacrificial material and a structural material as described above, two structural materials may be plated to form the layer 16 shown in FIG. 1C. For example, a titanium-nickel alloy and a stainless steel may form the layer 16.

Alternatively, in one embodiment of the invention, and with continued reference to FIG. 1C, the layer 16 may be constructed by plating a layer of material as described above with respect to FIG. 1A. However, rather than blanket plating a second material over the pattern 14 (as shown in FIG. 1B), a mask (not shown) may be used to selectively expose one or more of the exposed areas 22a, 22b (shown in FIG. 1A) during plating of the second material. The mask may prevent the second material from being plated on the pattern 14. In this manner, selected exposed regions 22a, 22b may be "filled" with a pattern of the second material. The pattern of the second material may completely fill the respective exposed areas 22a, 22b or fill only a portion thereof depending on the configuration of the mask.

For example, the layer 16 depicted in FIG. 1C may be formed by masking the pattern 14 and then plating the structural material 26 in one or both of the exposed areas 22a, 22b. It will be appreciated that plating may include plating a second and a third material into exposed areas 22a, 22b, respectively. Furthermore, multiple additional materials may be plated depending on the number of exposed areas and the orthodontic appliance design. Due to the use of a mask or other device to selectively plate in exposed areas, a planarizing step may not be needed.

In more detail, according to one embodiment, the method may include exposing the substrate 12 to a first plating solution. A mask (not shown) may then be placed proximate the substrate 12 to define a first exposed area between the mask and the substrate 12. Plating a first material from the first plating solution on the substrate may include plating in the first exposed area to form a first pattern 14 having a first perimeter. The mask may then be removed and a second mask (not shown) may be used to plate a second material in exposed areas determined by the second mask. This may include plating a pattern of the second material proximate the first pattern, such as, in the same layer. It will be appreciated that the first and second patterns may be in direct contact with one another, though embodiments of the present invention are not limited thereto.

While the initial material is described above as being a sacrificial material, it will be appreciated that the reverse construction is also possible. In other words, a pattern of the structural material may initially be plated on the substrate 12 and the sacrificial material may then be selectively deposited or blanket deposited on or in the pattern of the structural material to form a layer containing patterns of two materials.

Figure 1D:
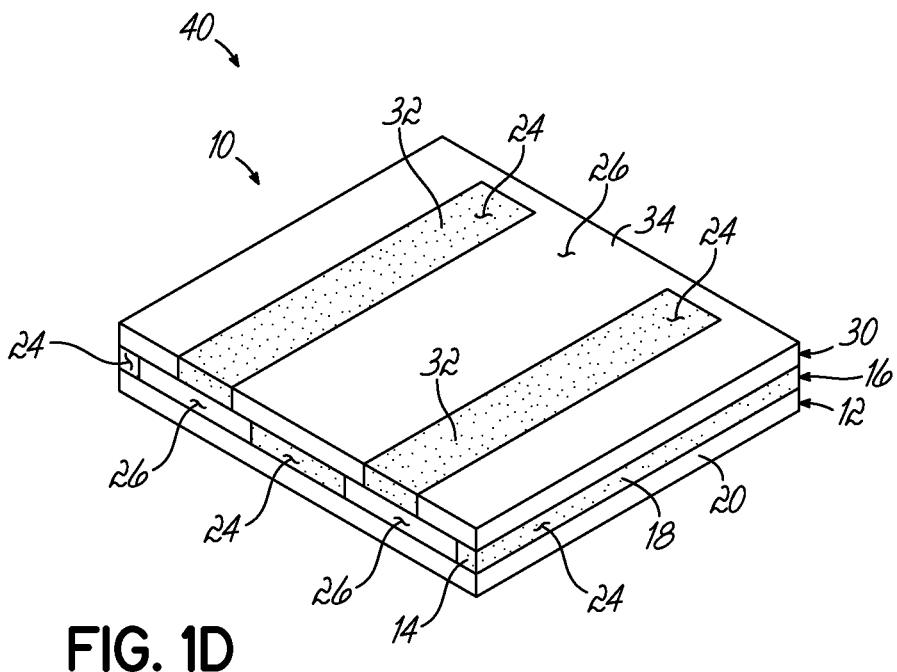
FIG. 1D is a perspective view illustrating a second layer of two different materials individually plated on the layer depicted in FIG. 1C.

As is briefly described above, repeating plating of a pattern of one or more of materials builds up the layered structure 10. With reference now to FIG. 1D, following blanket plating and planarizing, if required, a second layer 30 may be plated onto the layer 16. The second layer 30 may include one or more patterns 32 of a sacrificial material and one or more patterns 34 of a structural material in a similar plating process to that described above. However, where the desired design includes one or more of an undercut, an overhang, a recess, or a cavity or a combination thereof, pattern 34 of the structural material may reside completely on or overlap the pattern 14 of the sacrificial material 24 of layer 16 or otherwise extend onto the pattern 14 in at least one location as shown. Thus, the sacrificial material 24 supports an overlapping portion of the pattern 34 of the structural material. It will be appreciated that the presence of the sacrificial material allows design features that are not capable of being formed by other processes to be constructed according to embodiments of the present invention. By way of additional example, exemplary features that may be constructed include slots, curved and non-circular holes and channels, thin walled structures, and sharp corners.

Once plating of each of the layers 16, 30 according to a predetermined design is complete, a resulting assembly 40 may include the layered structure 10 together with any sacrificial material, such as in patterns 14 and 32. This sacrificial material may be then removed from the assembly 40 to release the layered structure 10 for use. As set forth above, removing the sacrificial material may include melting, etching, or dissolving the sacrificial material. Exemplary removal processes may include heating the assembly to a temperature above the melting temperature of the sacrificial material but below a detrimental temperature (e.g., the melting temperature) of any of the structural materials in the layered structure 10. Alternatively, by way of additional example, removing may include immersing the layered structure 10 in a solvent or etchant that selectively removes the sacrificial material.

Figure 1E:
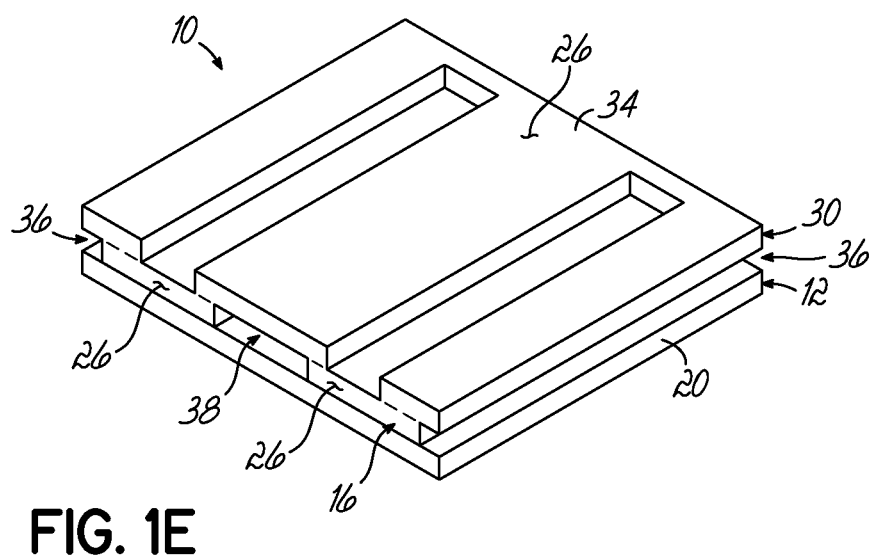
FIG. 1E is a perspective view of the two layers of FIG. 1D following removal of one of the materials from both layers.

As shown in FIG. 1E, once the patterns 14 and 32 of sacrificial material are removed, the layered structure 10 may include one or more overhangs 36 and/or a recess or cavity 38. It will be appreciated that the layered structure 10, when made of a single structural material, may or may not exhibit visible stratification of the layers. In other words, the layered structure 10 may appear to be uniform. However, visible "stair steps" may be observed, usually under magnification, where the perimeters of the patterns of adjacent layers do not substantially align. It will be appreciated that the capability of making features, such as, an overhang 36 or a cavity 38, may expand the manufacturable design possibilities of many orthodontic appliances. In essence, making designs impossible to manufacture via conventional manufacturing techniques possible according to embodiments of the invention.

Following removal of the sacrificial material, the layered structure 10 may be further processed. Though the subsequent processes may not be required, subsequent processes may include polishing or finishing the surface of the layered structure 10 by a tumbling process or by contacting the surfaces of the layered structure 10 with a fine abrasive to remove any exposed sharp edges or other surface blemishes, if any. The substrate 12 may or may not be removed depending on the design. It will be appreciated that the thickness of the layers may dictate whether any finishing is required.

As introduced above, an orthodontic appliance may include multiple parts. Further, each part may move relative to and/or movably engage the remaining parts of the appliance during orthodontic treatment. That is, the parts may be coupled together. However, unlike prior art multipart appliances, according to one embodiment of the invention, the parts are coupled together during their formation rather than in a post-formation assembly process. In addition, multipart appliances according to embodiments of the invention may be made of multiple structural materials. However, the structural materials in each part may be the same or they may be different. In one embodiment, each part is made of a different structural material. As set forth below, exemplary orthodontic appliances that may be made by the repetitive plating operation described herein are shown in FIGS. 2A-6B.

Figure 2A:
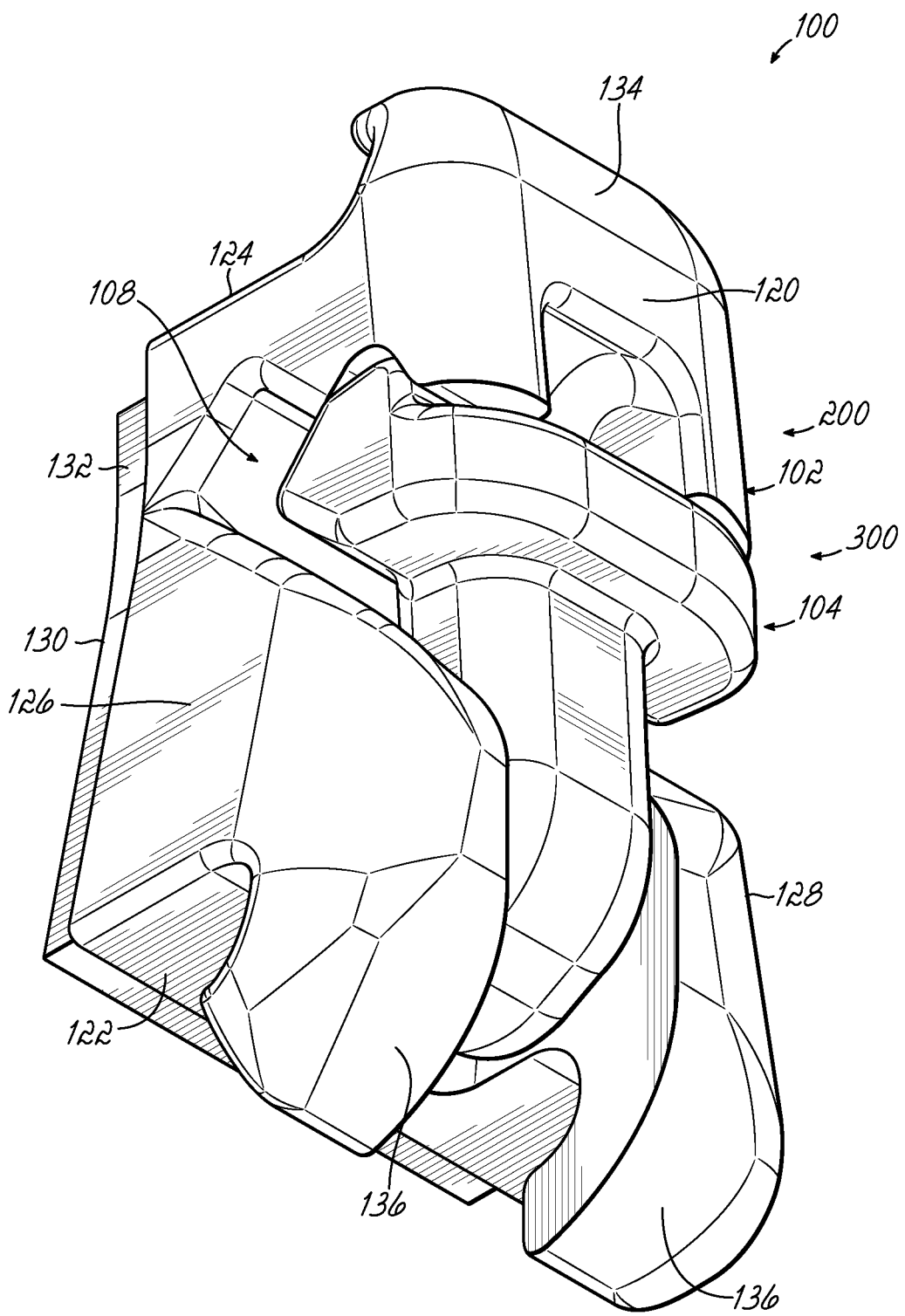
FIG. 2A is a perspective view of a self-ligating orthodontic bracket with a ligating latch in the closed position according to one embodiment of the invention.
Figure 2B:
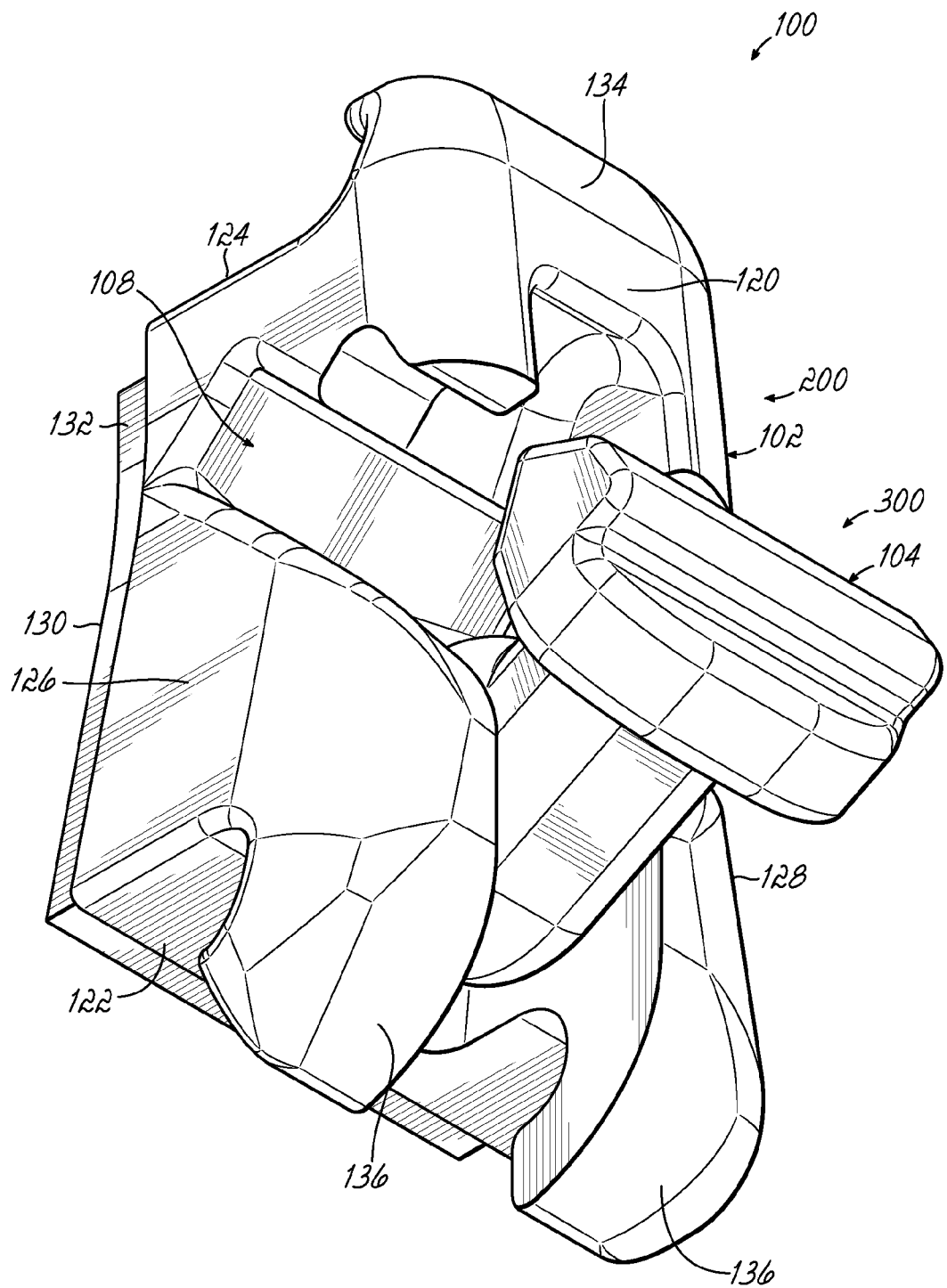
FIG. 2B is a perspective view of the orthodontic bracket shown in FIG. 2A with the ligating latch in the open position.

With reference now to FIGS. 2A-3C, in one embodiment of the invention, multiple layered structures are formed in their respective operable positions such that they are configured as a self-ligating orthodontic bracket 100, as shown in FIGS. 2A and 2B. The bracket 100 is similar to the self-ligating brackets disclosed in U.S. Provisional Application No. 61/381,868 ("the '868 application"), filed Sep. 10, 2010, which is incorporated by reference herein in its entirety. Any of the self-ligating brackets disclosed in the '868 application may be made according to embodiments of the invention. Alternative orthodontic brackets that may be made according to embodiments of the invention include, but are not limited to, the self-ligating brackets disclosed in U.S. Pat. No. 7,674,110 and in U.S. application Ser. No. 12/147,877, which are also incorporated by reference herein in their entireties.

With reference to FIGS. 2A and 2B, the bracket 100 may differ from that shown and described in the '868 application in a number of features when it is constructed in a manner set forth herein. These differences are described below. However, as a consequence of one or more of these differences, the manufacturability and clinical performance of the bracket 100 may be significantly improved.

Figure 3A:
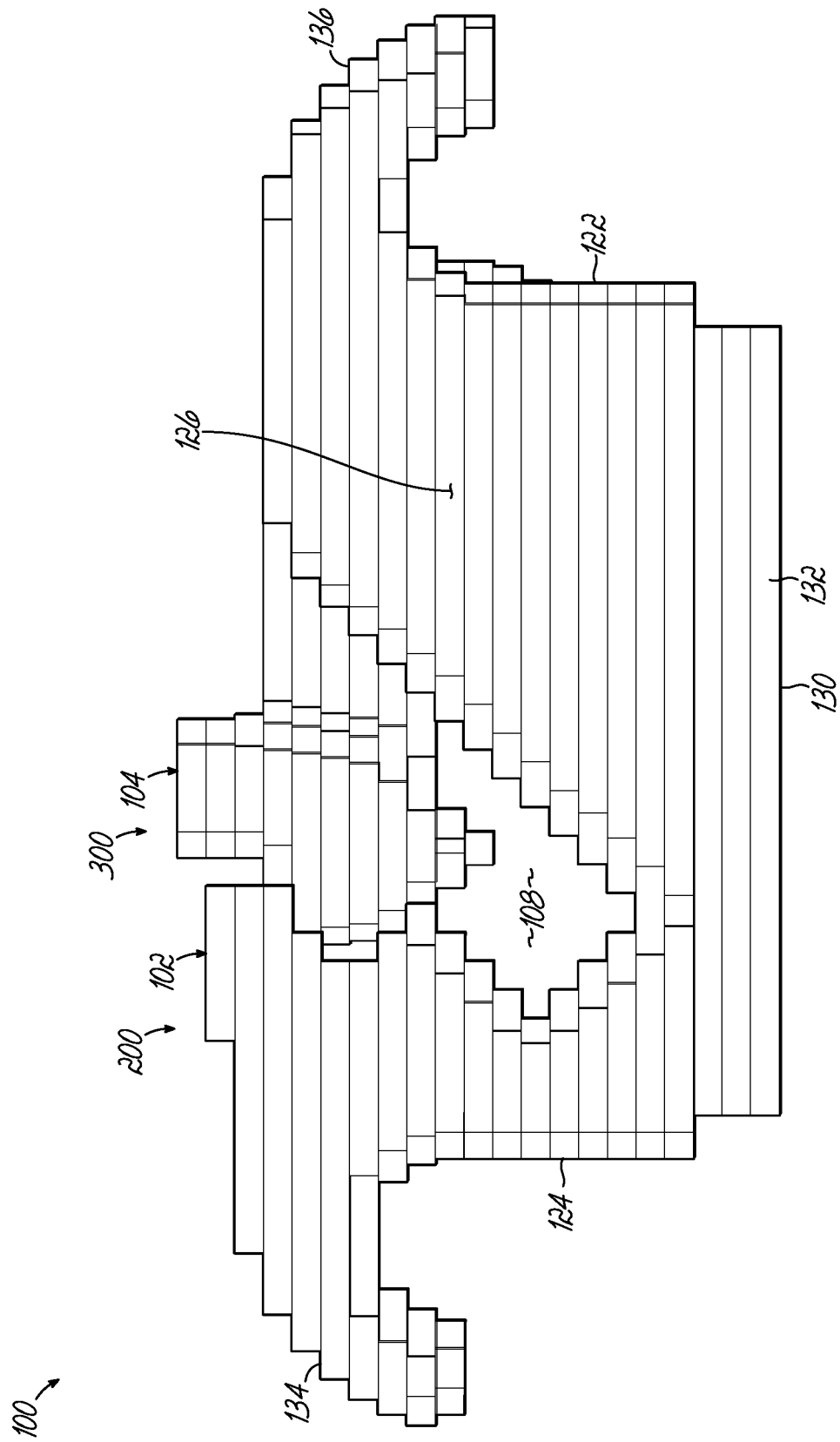
FIG. 3A is a side elevation view of the orthodontic bracket of FIG. 2A depicting layered structures according to one embodiment of the invention.
Figure 3B:
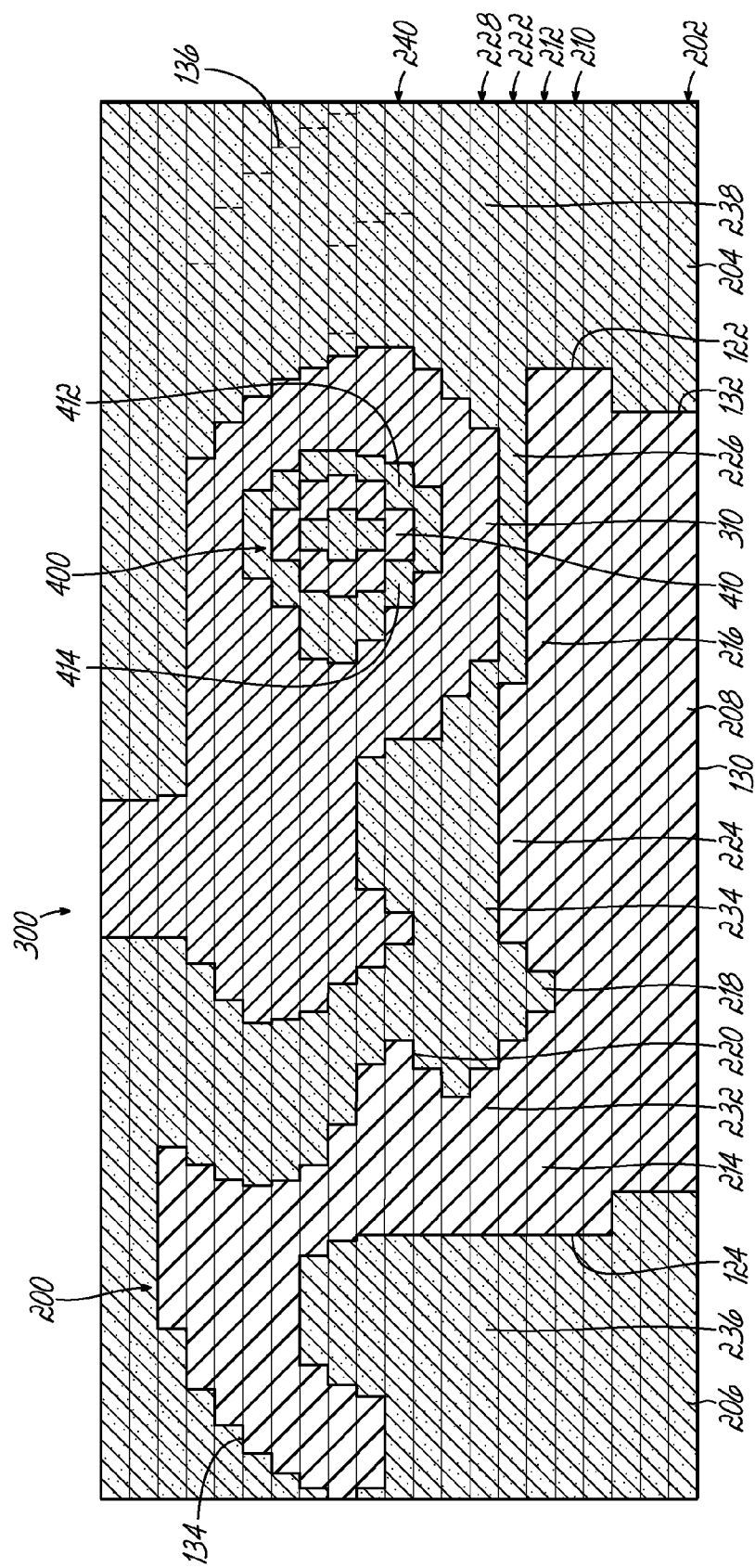
FIG. 3B is a cross-sectional view of the layered structures of FIG. 3A prior to removal of a sacrificial material.
Figure 3C:
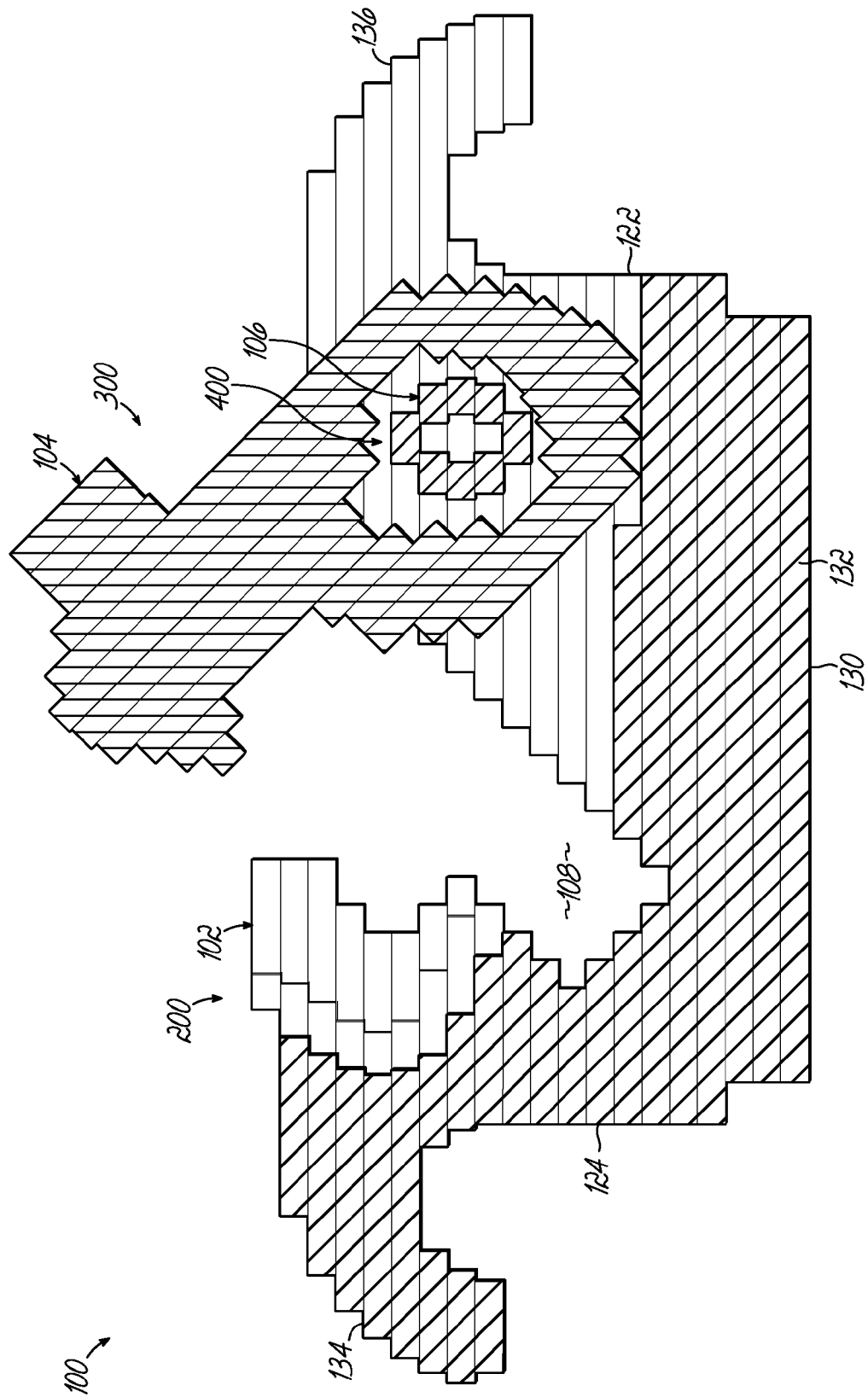
FIG. 3C is a cross-sectional view of the layered structures of FIG. 3A following removal of the sacrificial material depicted in FIG. 3B and illustrating the ligating latch rotated toward an open position.
Figure 4:
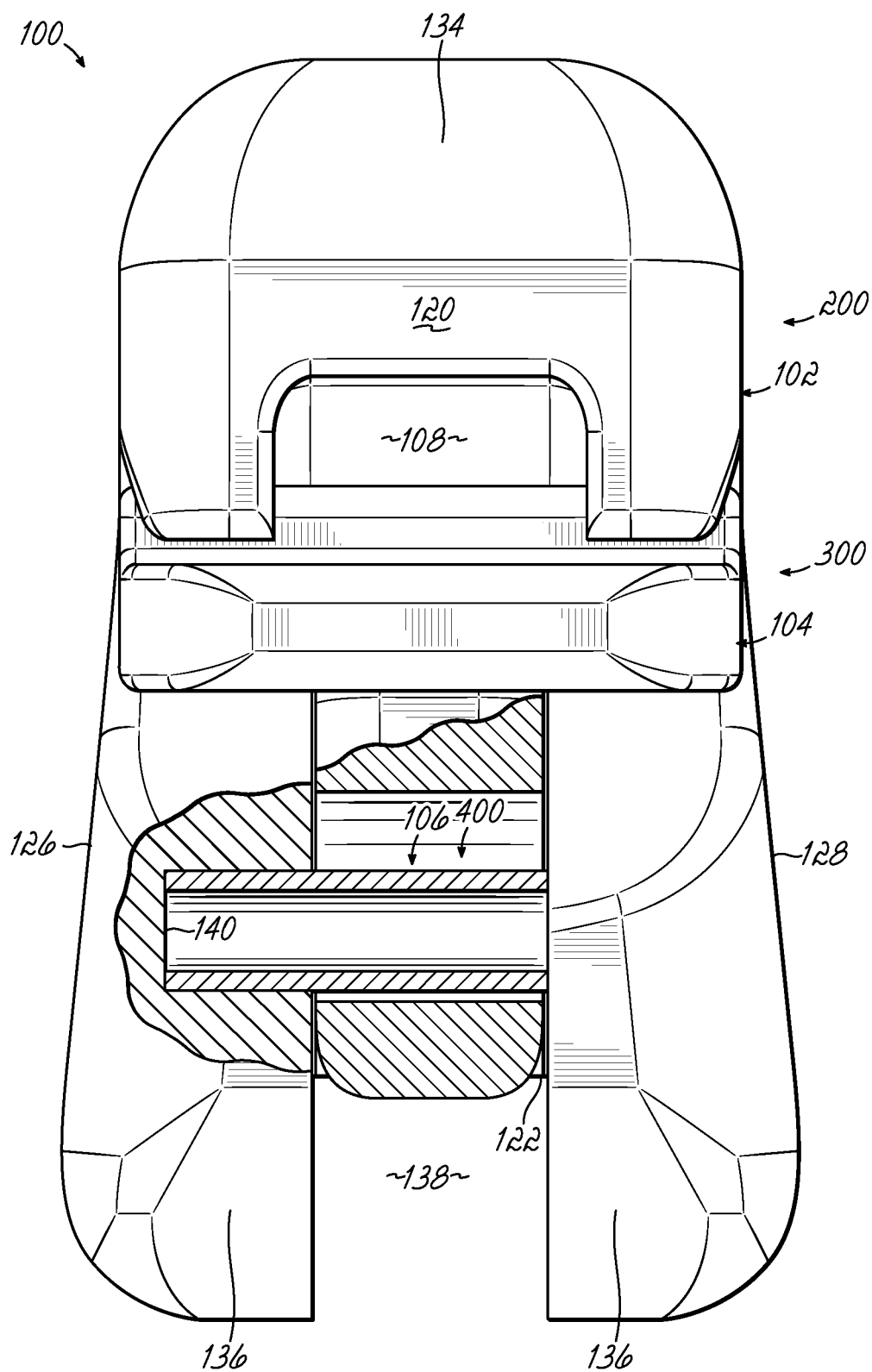
FIG. 4 is a partial-sectional view of the orthodontic bracket shown in FIG. 2A according to one embodiment of the invention.
Figure 5:
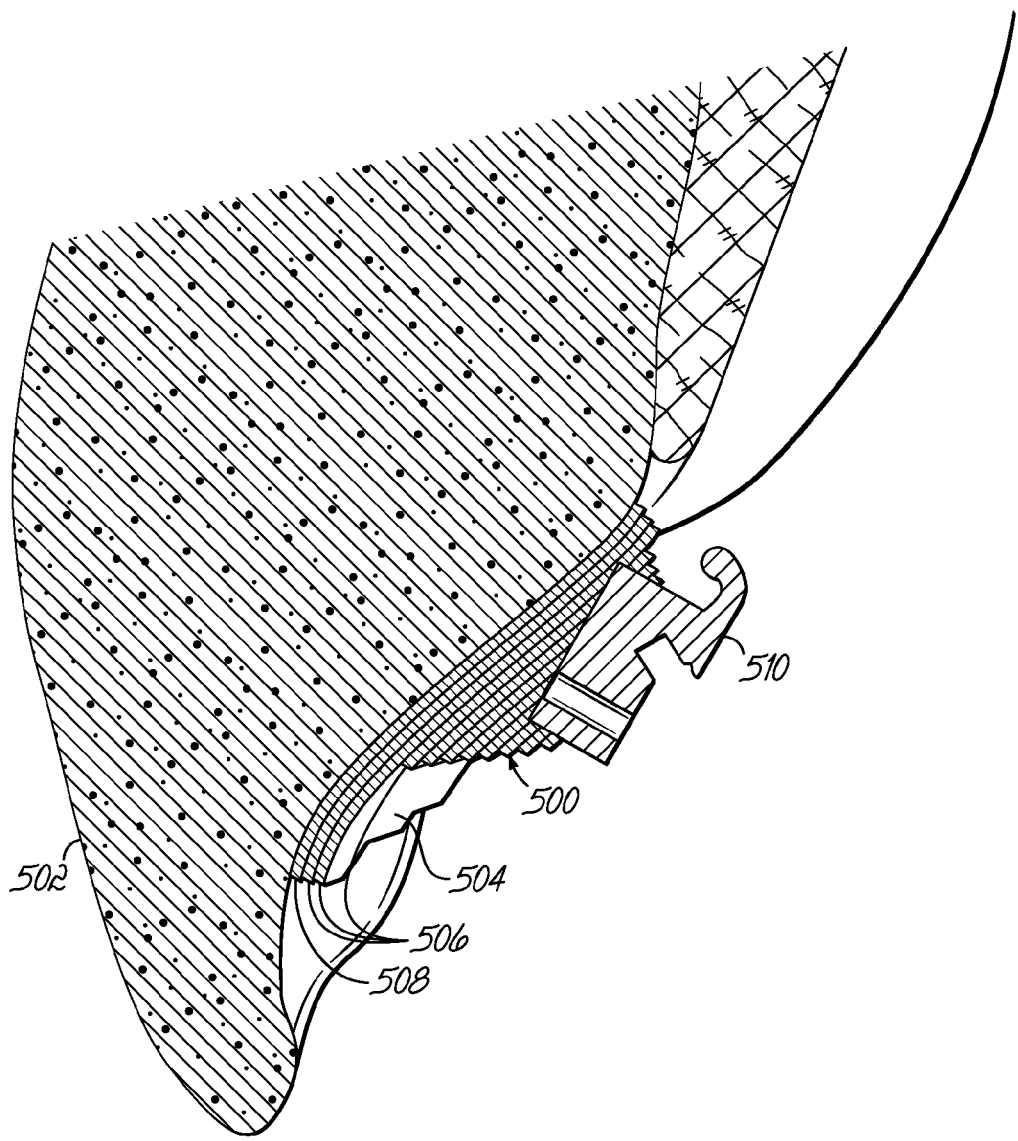
FIG. 5 is a cross-sectional view of an orthodontic pad according to one embodiment of the invention that is secured to a tooth.

In the embodiment shown in FIGS. 2A and 2B, the bracket 100 is constructed of three layered structures that include a first layered structure 200 that may be configured as a bracket body 102, a second layered structure 300 that may be configured as a movable member, such as, a ligating latch 104, and a third layered structure 400 that may be configured as a resilient hinge pin 106 (shown in FIGS. 3B, 3C, and 4). Each of the layered structures 200, 300, 400 may be formed in place relative to one another.

The features and functions of the bracket body 102, latch 104, and pin 106, but for the differences described herein, are disclosed in the '868 application. However, to facilitate the description herein, the bracket body 102 includes an archwire slot 108 that is adapted to receive an archwire (not shown) for applying corrective forces to a tooth. The latch 104 is movable between a closed position (FIG. 2A) in which the latch 104 retains the archwire within the archwire slot 108 and an open position (FIG. 2B). The latch 104 may be securely held in the open and the closed positions by interaction with the resilient hinge pin 106 (shown in FIGS. 3B, 3C, and 4). The hinge pin 106 thus defines a pivot point or hinge around which the latch 104 may rotate and may allow the latch 104 to translate to a limited degree transversely to the archwire slot 108.

Additionally, the orthodontic bracket 100 may be configured for use on the lingual surface of an anterior tooth on the upper jaw. In this regard, the overall shape and profile of the orthodontic bracket 100 generally corresponds to the shape of anterior teeth on the upper jaw. When mounted to the lingual surface of an anterior tooth (not shown) carried on the patient's upper jaw, the bracket body 102 has a lingual side 120, an occlusal side 122, a gingival side 124, a mesial side 126, a distal side 128, and a labial side 130. The labial side 130 of the bracket body 102 is configured to be secured to the tooth in any conventional manner. The labial side 130 may include a shaped projection 132 configured for insertion and coupling with a corresponding receptacle formed on a pad (not shown) and defining a bonding base that is secured to the surface of the tooth. The bracket body 102 further includes a single gingival tie wing 134 and a pair of occlusal tie wings 136.

As introduced above, the latch 104 and resilient hinge pin 106 are each manufactured in place or coupled during manufacturing of each individual part of the bracket body 102. More specifically, and as shown in FIGS. 3A-3C, each of the first, second, and third layered structures 200, 300, 400 are manufactured concurrently with one another. That is, portions of each layered structure 200, 300, 400 may be plated in the same layer as portions of the other two structures. Thus, patterns of the material for the first layered structure 200 may occupy the same layer as patterns for each of the second layered structure 300 and third layered structure 400. Once these structures are formed and following removal of the sacrificial material and subsequent to any finishing operation, the layered structures 200, 300, 400 form the orthodontic bracket 100. For convenience of description of an exemplary manufacturing process for the bracket 100, reference may be made to various features of the orthodontic bracket 100 in conjunction with the layered structures 200, 300, 400. However, such references are not intended in any way to limit any embodiments of the invention.

By way of example, in the embodiment shown in FIGS. 3A-3C, the design is predetermined to contain layers that may be substantially parallel to the labial side 130 of the design of the bracket body 102. However, as set forth above, the direction of the "slicing" of the design into layers is predetermined and may differ significantly from that shown in FIGS. 3A-3C. For example, the selected direction of the layers may be at an angle, for example, about 90 degrees, relative to that shown.

The number of layers that the design may be sliced into may also vary. While FIGS. 3A-3C depict twenty-one layers in all, it will be appreciated that the number of layers may be dictated by the overall dimensions of the orthodontic appliance, the thickness of the individual layers, the sizes of the features formed thereby, and the desired smoothness of the surfaces, among other factors. In addition, while all of the layers are depicted as being uniform in thickness, embodiments of the invention are not limited to those having uniformly thick layers. For example, the shaped projection 132 may be formed with a single thicker layer rather than with three thinner layers, as shown. The remaining layers of each structure 200, 300, 400 may be thicker or thinner depending on the desired features or functions of the bracket 100.

With further regard to the individual layer thicknesses, it will be appreciated that adding layers, that is making each layer thinner, for a given size orthodontic appliance, may allow finer features to be formed and may also create a finer surface finish. Selection of the number of layers with which to manufacture an orthodontic appliance may be predetermined and may ultimately depend on cost, performance, and other factors. Furthermore, the order in which the layers are plated may be changed depending on the orthodontic appliance design in question. For example, rather than initiating the plating process with the shaped projection 132 as is described below, an exemplary plating process as described herein may begin with the second layered structure 300 which forms the latch 104 and end with the first layered structure 200 at the shaped projection 132.

Collectively, in FIGS. 3A-3C and by way of example only, the number of overall layers is twenty-one. Individually, the bracket body 102 is segregated or sliced to include twenty layers, the latch 104 includes fourteen layers, and the pin 106 includes six layers. Each of the body 102, latch 104, and the pin 106 may be made of the same or different materials. By way of example, the body 102 and latch 104 may be made of the same non-resilient structural material, such as, 17-4 stainless steel. The pin 106, however, may be made of a nickel-titanium (NiTi) alloy having superelastic and/or shape memory material properties.

In view of the above and with reference to FIG. 3B, an exemplary layering process may include plating a first layer 202 of the first layered structure 200 including patterns 204, 206 of a sacrificial material and a pattern 208 of a structural material on a substrate (not shown). The pattern 208 of the structural material in the first layer 202 begins the formation of the first layered structure 200. The pattern 206 of the sacrificial material is plated to support the layers of the first layered structure 200 that define the tie wing 134 during plating of the layers that define the tie wing 134. The pattern 204 of the sacrificial material may or may not be used to support plating layers that define the tie wings 136 (shown in FIG. 3A).

The plating or stacking of subsequent layers after the first layer 202 may continue with each subsequent layer containing one or more patterns of the sacrificial material and a pattern of the structural material. Each subsequent pattern of structural material may overlap the previous pattern of structural material. For the first layer 202 through the fifth layer 210, the overlapping of the patterns of the structural material builds a portion of the bracket body 102 including the projection 132. In this instance, the first layered structure 200 up to the archwire slot 108 is formed by the first five layers.

With continued reference to FIG. 3B, plating a sixth layer 212 includes plating two separate patterns 214, 216 of the structural material that are separated by a pattern 218 of sacrificial material. The intervening pattern 218 of the sacrificial material is positioned to support the eventual layering of the latch 104.

During plating of a seventh layer 222, a pattern 224 of the structural material may not extend to the occlusal side 122 of the bracket body 102. Rather, the pattern 224 may abut a pattern 226 of the sacrificial material that extends past the occlusal side 122 of the bracket body 102. The pattern 226 of sacrificial material may also separate a subsequent plated layer of the structural material of the latch 104 from the structural material of the bracket body 102.

Further plating of layers including patterns of structural material separated by a pattern of sacrificial material defines the archwire slot 108 (shown in FIG. 3A). It will be appreciated that an overhang 220 that defines a portion of the archwire slot 108 is supported by the sacrificial material separating the structural material patterns on the occlusal and gingival sides thereof.

During plating of an eighth layer 228, patterns for each of the first layered structure 200 and the second layered structure 300 are plated. For instance, in the eighth layer 228, a pattern 310 of structural material of the latch 104 and a pattern 232 of structural material of the bracket body 102 are separated by a pattern 234 of sacrificial material. The pattern 232 is spaced apart from the pattern 234. Further in this regard, the eighth layer 228 may include patterns of three different materials, where the latch 104 is to be made of a different material than the bracket body 102. Specifically, as shown in the FIG. 3B, the eighth layer 228 includes a pattern 236 of sacrificial material to support plating of the tie wing 134, the pattern 232 structural material of the bracket body 102 to define the gingival side 124 and archwire slot 108 of the bracket body 102, the pattern 234 of the sacrificial material, the pattern 310 of structural material of the latch 104, and a pattern 238 of the sacrificial material which may support the layers that eventually define the tie wing 136. As is illustrated by layer 228, a pattern of structural material may be plated entirely on a previously plated pattern of sacrificial material (e.g., pattern 310 is plated entirely on the pattern 226 of layer 222). That is, the sacrificial material may be selectively positioned to separate the structural materials of each layered structure 200, 300, 400.

During plating of the eleventh layer 240, portions of the three layered structures 200, 300, 400 are each formed. So, the layer 240 includes patterns of structural material of the bracket body 102, patterns of structural material of the latch 104, a pattern 410 of structural material of the pin 106 with each material (i.e., the material of the pin 106 and the material of the latch 104) separated by patterns 412, 414 of sacrificial material. Layers twelve through fifteen each also include portions of all three layered structures 200, 300, 400. Once the layered structure 400 configured as the pin 106 is formed, the plating process reverts to the structural materials of the latch 104 and body 102 until the first layered structure 200 is complete. The remaining two layers complete the second layered structure 300.

As noted above, sacrificial material separates the latch 104 from the pin 106 and the latch 104 from the bracket body 102. Although not shown, the pin 106 and the bracket body 102 may be in an abutting relationship such that during operation, the pin 106 may not rotate. In this regard, during plating, a pattern of the structural material of the bracket body 102 and a pattern of the structural material of the pin 106 are in direct contact. That is, they are neither spaced apart from one another nor are they separated by a sacrificial material.

Once each of the layered structures 200, 300, 400 is complete, the sacrificial material is removed. As depicted in FIG. 3C, the layered structures 200, 300, 400 are then free to be moved relative to one another. Accordingly, the layered structures 200, 300, 400 may form the orthodontic bracket 100. The latch 104 may be rotated toward the open position, as shown in FIG. 3C. In addition to allowing the latch 104 to rotate relative to the hinge pin 106, the pin 106 may flex to allow the latch 104 to move longitudinally with respect to the bracket body 102. Advantageously, no post formation assembly of the latch 104 and pin 106 with the bracket body 102 is required as each of these is formed in their respective, relative operational positions. The orthodontic bracket 100 may be ready for immediate use.

According to embodiments of the invention and with reference to FIG. 4, the bracket body 102 includes a blind hole, recess, or enclosed bore 140 in each side portion thereof. In other words, the bracket body 102 may close off each end portion of the bore 140, though the body 102 is a single unitary body. In one embodiment, there is no bore extending entirely through the bracket body 102. The absence of such a through-bore is advantageous, because one avenue for ingress of food and debris that may interfere or prevent the latch 104 from operating properly is eliminated. Each side portion of the bore 140 intersects and may be open to a central space 138.

In one embodiment shown in FIG. 4, the pin 106 is formed in place or coupled to each side portion of the bore 140 and extends through the latch 104. As set forth above, there is thus no need to separately insert a preformed pin into the bore 140 because the hinge pin 106 is formed during the plating process described above. Furthermore, the pin 106 may be intimately engaged with the bracket body 102 in the bore 140. Consequently, the pin 106 may not slide or rotate relative to the bracket body 102. Additionally, the intimate or abutting relationship of the pin 106 and the bracket body 102, due to abutting patterns of each material in the respective layers, may further reduce ingress of potentially damaging food and other debris between the pin 106 and the bracket body 102. Embodiments of the invention are not limited solely to one, two, or three layered structures. Additional layered structures may be coupled to those described above. For example, a layered structure in the configuration of an orthodontic hook (not shown) may be integral with the layered structure 200 and extend from the bracket body 102. The hook may facilitate coupling of the bracket body 102 with other orthodontic elements, such as bands or other hooks on adjacent teeth. It will be appreciated that including a hook, either as a portion of the layered structure 200 or as a separate structure, may eliminate post formation welding or a similar process. It will also be appreciated that other multipart orthodontic appliances in addition to orthodontic brackets may be made according to the methods described herein.

As briefly described above, with reference now to FIG. 5, in one embodiment of the invention, a pad 500 may be custom formed to fit a specific surface of a tooth 502. In the embodiment shown, the pad 500 is configured to attach to a lingual surface of an upper anterior tooth. However, the pad 500 may be custom fit a specific, preselected tooth surface. In one embodiment, the pad 500 is formed of a layered structure 504. The layered structure 504 is formed by plating individual layers 506 of a structural material on a substrate (not shown), as is described in detail above. Accordingly, where the substrate is a replica of a patient's tooth, at least the initial layer 508 may conform to the substrate and thus be a custom fit for the patient's specific tooth. The substrate may be made by taking impressions of the patient's tooth. The impressions may be scanned or digitized for manipulation with a computer. The substrate may then be made from the scanned or digitized information.

Once the layered structure 504 is formed, and any additional finishing operations are complete, the resulting pad 500 may be attached to a standard or off-the-shelf bracket body 510. That is, the pad 500 may be coupled to the bracket body 510 as a separate piece or element (e.g., by a welding process). Alternatively, although not shown, a bracket body may be plated onto the layered structure 504 in the same or in a separate plating process, as set forth above. In this regard, the layered structure 504 may function as the substrate for building another layered structure in the configuration of a bracket body.

Figure 6:
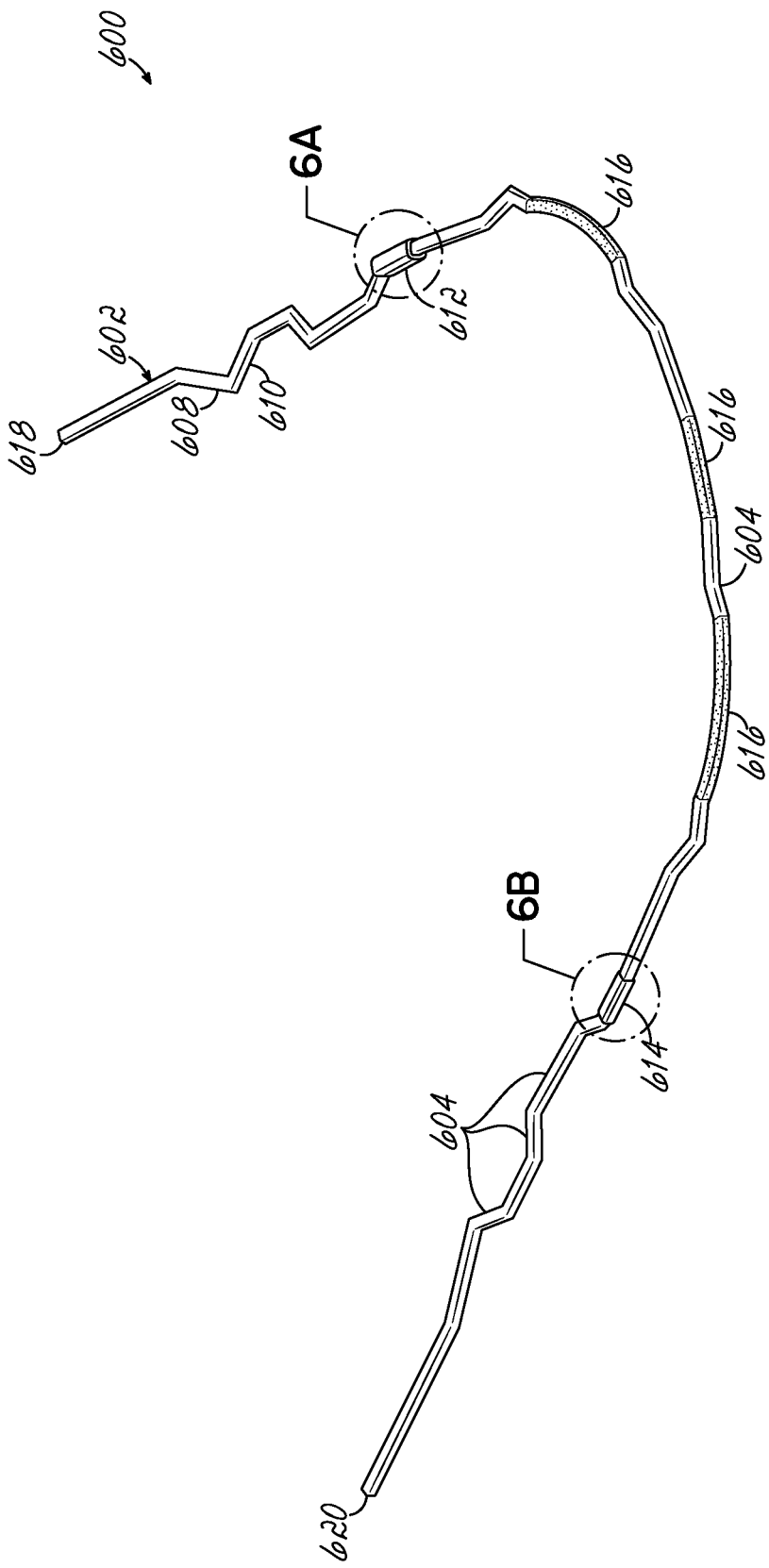
FIG. 6 is a perspective view of an orthodontic archwire according to one embodiment of the invention.
Figure 6A:
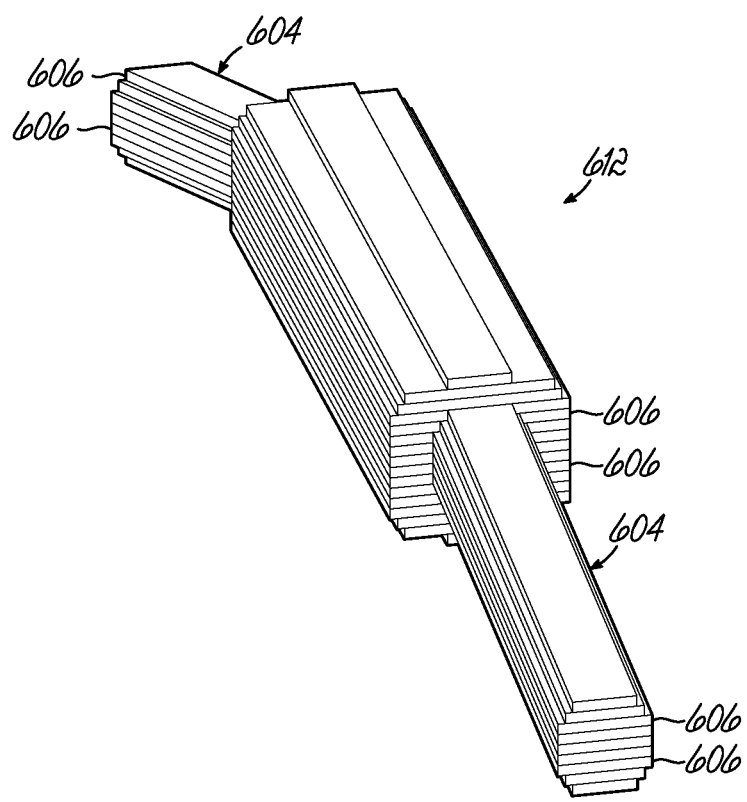
FIGS. 6A and 6B are enlarged perspective views of encircled areas 6A and 6B, respectively, of the orthodontic archwire of FIG. 6.
Figure 6B:
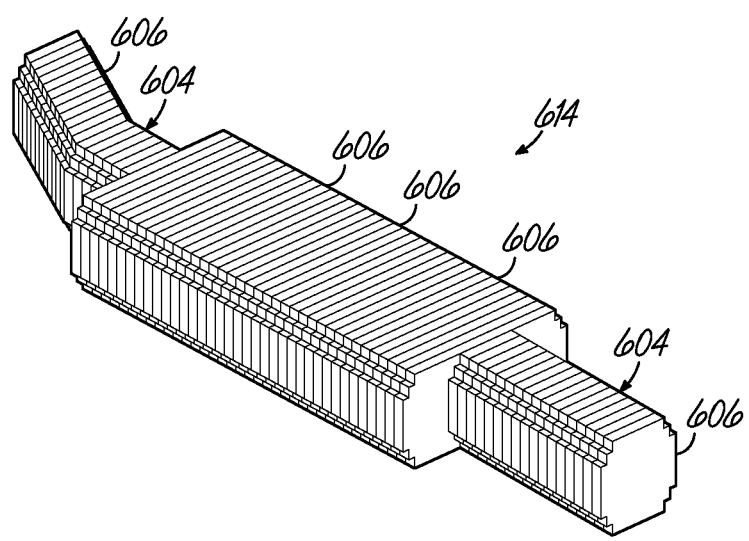

In one embodiment of the present invention and with reference to FIGS. 6, 6A, and 6B, a layered structure 600 may be constructed according to one embodiment of the invention described above in the form of an orthodontic archwire 602. The layered structure 600 may be a uniformly arched, or unbent, configuration similar to an off-the-shelf archwire (not shown) or may be formed of multiple sections 604, as shown in FIG. 6. Each section 604 may be a stack of multiple layers 606 (shown in FIGS. 6A and 6B). In one embodiment, two adjacent sections 608 and 610 may form an angle between their respective longitudinal axes or appear to be bent relative to one another. The angle between the sections 608 and 610 may be predetermined prior to manufacturing of the layered structure 600. Thus, the angle may be included during the construction of the layers 606. In one embodiment, the sections 608 and 610 are positioned relative to one another according to a prescription for a specific patient. In other words, the shape, including any bends, of archwire 602 may be customized according to a specific treatment methodology on a patient-by-patient basis. Accordingly, no post-formation bending of the archwire 602 may be required.

In addition or as an alternative to the above, one or more of the sections 604 may be of a smaller or larger cross-sectional configuration. For example, section 612, which is shown best in FIG. 6A, has a larger cross sectional area than either of the adjacent sections 604, though the shape of the cross section may be similar. However, the cross-sectional shape of the layer structure 600 may also vary by or within each section 604. For example, section 614, which is shown best in FIG. 6B, has a different cross-sectional configuration or shape than adjacent sections 604.

The layered structure 600 may also vary in composition along its length. For example, as depicted in FIG. 6, sections 616 may be constructed of a different material than any adjacent section 604. By way of specific example, the layered structure 600 may contain one or more sections of stainless steel and other sections of NiTi at predetermined locations along the length of the archwire 602. Advantageously, no heat is required to create this combination of materials. Again, the predetermined locations may be to facilitate a particular treatment on a specific patient. It will be appreciated that one or more of the combination of size, shape, and material may improve orthodontic treatment by reducing treatment time.

With reference to FIGS. 6A and 6B, it will be appreciated that the layers 606 of the layered structure 600 may be oriented relative to the overall orientation of resulting archwire 602. By way of example, as shown in FIG. 6A, the layers 606 may be plated generally in the plane of the resulting archwire. The layers 606 may thus be substantially parallel to the longitudinal axis of the archwire 602. In this instance, one or more of the layers 606 may extend over the entire length of the layered structure 600. In other words, one or more of the layers 606 may be continuous from one end 618 to the other end 620 of the layered structure 600 (labeled in FIG. 6). However, any one of the layers 606 may be limited to a particular section 604. By way of alternative example, as shown in FIG. 6B, the layers 606 may be oriented perpendicular to the plane of the resulting archwire in which case none of the layers 606 may extend over the entire length of the layered structure 600. The layers 606 may thus be substantially perpendicular to the longitudinal axis of the archwire 602. However, other orientations are possible as described above.

Other orthodontic appliances may be manufactured according to the embodiments of the invention described herein. For example, a Temporary Anchoring Device (TAD) (not shown) is a miniature screw positioned in the mouth. A TAD serves as an anchor for moving specific teeth. Devices incorporating miniature screws, including palatal expansion devices, molar distalization devices, as well as other devices using screws, and are disclosed in U.S. application Ser. No. 12/349,284, which is incorporated by reference herein in its entirety. While some TADs are made of a sterile medical-grade titanium alloy, a layered structure may be utilized to transition a titanium screw portion of the TAD to an abutment made of a shape memory alloy (e.g., NiTi). The flexure properties of such an abutment would facilitate ease of snapping an attachment on to the abutment. In another embodiment, the screw may be a dental implant in which case a similar construction may ease attachment of an artificial tooth to the abutment.

In still other embodiments of the present invention, one or more layered structures may form or be incorporated into a handheld orthodontic tool, a dental file, a spacer, a band, and a spring, to name only a few.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. A method of manufacturing a self-ligating orthodontic bracket having at least a bracket body and a movable member, comprising:
    exposing a substrate to a plating solution;
    plating a first pattern of a first material on the substrate from the plating solution to define a first layer; and
    repeating plating of the first material in direct contact with the first layer one or more times to form one or more additional patterns, at least one additional pattern defining a respective layer on at least one of the first layer or a layer applied subsequent to the first layer to build up a first layered structure that forms at least a portion of the bracket body.

2. The method of claim 1, further comprising:
    exposing the substrate or the first material to a second plating solution; and
    plating a second pattern of a second material from the second plating solution on the substrate or on the first material, the second material being different from the first material.

3. The method of claim 2, wherein the first material is a sacrificial material and the second material is a structural material, the method further comprising:
    following forming of the first layered structure, removing the sacrificial material whereby the structural material forms the portion of the bracket body.

4. The method of claim 3, wherein removing the sacrificial material forms at least one of an undercut, an overhang, a recess, or a cavity or a combination thereof in the portion of the bracket body.

5. The method of claim 2, further comprising:
remove a portion of one or both of the first and second materials to expose portions of each of the first and second materials in one layer.

6. The method of claim 5, wherein repeating plating of the first material includes plating a third pattern of the first material on portions of the first and second materials.

7. The method of claim 1, wherein the first material is a metal and plating includes electroplating the metal.

8. The method of claim 1 wherein a perimeter of the first pattern or a perimeter of the one or more additional patterns defines a surface portion of the bracket body.

9. The method of claim 1, wherein the substrate forms a portion of the bracket body.

10. The method of claim 1, wherein the bracket body includes an orthodontic pad and the layered structure defines a bonding surface of the pad that is configured to be attached to the surface of a preselected tooth.

11. The method of claim 1, wherein the method further comprises:
exposing the substrate or the first material to a second plating solution;
plating a pattern of a second material from the second plating solution on the substrate or on a pattern of the first material; and
repeating plating of the second material one or more times to form one or more additional patterns to build up a second layered structure that forms at least a portion of the movable member, wherein plating patterns of the second material includes plating at least one pattern of the second material in a layer that is common to both of the bracket body and the movable member so as to form the movable member in place relative to the bracket body.

12. The method of claim 11, wherein plating patterns of the second material includes plating patterns of the second material spaced apart from the patterns of the first material.

13. The method of claim 11, further comprising:
plating a sacrificial material between at least one pattern of the first material and at least one pattern of the second material, whereby the first layered structure and the second layered structure are separated by the sacrificial material; and
removing the sacrificial material following forming of each of the first and second layered structures.

14. The method of claim 11, wherein the orthodontic bracket includes a spring mechanism or a hinge mechanism, the method further comprising:
plating a plurality of patterns of a third material, the collective patterns of the third material defining a third layered structure that forms the spring mechanism or the hinge mechanism that couples the bracket body to the movable member.

15. The method of claim 14, wherein plating patterns of the third material includes plating at least one pattern of the third material directly in contact with a pattern of the first material and plating at least one pattern of the third material directly in contact with a pattern of the second material such that the third layered structure is in direct contact with each of the first and second layered structures.

16. A method of manufacturing a self-ligating orthodontic bracket having at least a bracket body and a movable member, comprising:
plating a first pattern of a sacrificial material on a substrate to define a first layer;
plating a second pattern of a structural material on the substrate or on the first material;
repeating plating of at least one of the sacrificial material or the structural material in direct contact with the first layer one or more times to form one or more additional patterns, at least one additional pattern defining a respective layer on at least one of the first layer or a layer applied subsequent to the first layer to build up a first layered structure that forms at least a portion of the bracket body; and
removing the sacrificial material from the first layered structure by heating the first layered structure to a temperature above a melting temperature of the sacrificial material and below a detrimental temperature of the structural material whereby the structural material forms the portion of the bracket body.

* * * * *